United States Patent [19]
Bierman et al.

[11] Patent Number: 5,833,663
[45] Date of Patent: Nov. 10, 1998

[54] NASO-GASTRIC TUBE RETAINER

[76] Inventors: Steven F. Bierman, 143 Eighth St., Del Mar, Calif. 92014; Gregory M. Weiss, 3215 E. 1st St., Long Beach, Calif. 90803

[21] Appl. No.: 789,084

[22] Filed: Jan. 27, 1997

[51] Int. Cl.⁶ .................................................... A61M 5/32
[52] U.S. Cl. .................. 604/174; 604/180; 128/DIG. 26
[58] Field of Search .................................. 604/174, 100; 128/DIG. 26

[56] References Cited

U.S. PATENT DOCUMENTS

| | | |
|---|---|---|
| D. 243,477 | 2/1977 | Cutruzzula et al. . |
| D. 256,162 | 7/1980 | Haerr et al. . |
| D. 305,363 | 1/1990 | Gentelia et al. . |
| D. 310,414 | 9/1990 | Briggs, III . |
| D. 310,721 | 9/1990 | Beisang, III . |
| 2,748,766 | 6/1956 | Coates . |
| 3,046,989 | 7/1962 | Hill . |
| 3,529,597 | 9/1970 | Fuzak . |
| 3,556,096 | 1/1971 | Fuller et al. . |
| 3,677,250 | 7/1972 | Thomas . |
| 4,057,066 | 11/1977 | Taylor . |
| 4,120,304 | 10/1978 | Moor . |
| 4,133,307 | 1/1979 | Ness . |
| 4,142,527 | 3/1979 | Garcia . |
| 4,480,639 | 11/1984 | Peterson et al. . |
| 4,660,555 | 4/1987 | Payton . |
| 4,742,824 | 5/1988 | Payton et al. . |
| 4,823,789 | 4/1989 | Beisang, III . |
| 4,932,943 | 6/1990 | Nowak . |
| 4,976,700 | 12/1990 | Tollini . |
| 4,986,815 | 1/1991 | Schneider . |
| 5,037,397 | 8/1991 | Kalt et al. . |
| 5,135,506 | 8/1992 | Gentelia et al. . |
| 5,156,641 | 10/1992 | White . |
| 5,292,312 | 3/1994 | Delk et al. . |
| 5,295,950 | 3/1994 | Godley . |
| 5,468,231 | 11/1995 | Newman et al. . |
| 5,520,656 | 5/1996 | Byrd . |
| 5,533,499 | 7/1996 | Johnson . |
| 5,533,503 | 7/1996 | Doubek et al. . |

OTHER PUBLICATIONS

Four (4) photographs of Breathe–Rite™ strips: photocopy of Breathe–Rite™ package instructions (enlarged).
Beiersdoft, Inc. Ad: "A Toe Can Tell The Difference", *American Journal of Nursing*, Jul. 1977, p. 1117.
Beiersdoft, Inc. Ad: "A Finger Feels The Difference", *American Journal of Nursing*, Jul. 1977, p. 1119.

*Primary Examiner*—Wynn Wood Goggins
*Assistant Examiner*—N. Kent Gring
*Attorney, Agent, or Firm*—Knobbe, Martens, Olson & Bear, LLP

[57] ABSTRACT

An adhesive device retains a medical tube, and particularly a naso-gastric tube, in relation to a patient with improved flexibility, strength and adhesion. The device includes a nose pad portion for attaching to a patient's nose and a tube attachment section for attaching to the naso-gastric tube. A substantially inelastic spine extends across a narrow or otherwise vulnerable neck portion, which connects the nose pad to the tube attachment section. The spine strengthens the retaining device against tensile and shear forces while allowing flexibility. At the same time, deflection of the spine does not cause internal elastic stresses sufficient to counter adhesion of the retainer to either the patient or the medical tube.

28 Claims, 2 Drawing Sheets

NASO-GASTRIC TUBE RETAINER

BACKGROUND OF THE INVENTION

1. Field of the Invention

The present invention relates generally to devices for retaining medical and surgical tubes, and more particularly to devices for anchoring naso-gastric tubes to a patient's nose.

2. Description of Related Art

Medical tubes, such as catheters, are often required to provide an unobstructed passageway into the body of a patient for delivering or extracting fluids. Such tubes are often secured to the patient's body in order to prevent the tube from chafing and tearing at the patient's skin or tissue.

In naso-gastric applications, a naso-gastric tube is inserted into a patient's nostril and extended through the esophagus to the patient's stomach. Such tubes may be used for stomach pumping or feeding. In the latter case, the naso-gastric tube commonly is left in place for significant lengths of time, during which swallowing or other motion or patient movements tend to displace the tube relative to the patient. Movement of the tube often causes irritation to the nasal passages and the esophagus.

In the past, naso-gastric tubes have been adhered to the patient's nose with adhesive tape. Strips of tape are attached to the patient's face and extend to wrap around the naso-gastric tube. Stresses caused by motion of the tube or the patient, however, tend to cause tearing of the tape and/or detachment of the tape, necessitating frequent changing of the adhesive tapes.

In an effort to address the need to secure the naso-gastric tubing to the patient and to prevent tube migration from the patient's stomach, a variety of devices have been proposed. One such example is the device disclosed in U.S. Pat. No. 3,046,989, issued to Hill. The Hill patent describes a moldable aluminum sheet shaped with a narrow stem portion connecting a nose piece and a tab for attachment to the tube. The use of aluminum provided increased strength to the device; however, the aluminum reduced the device's flexibility which discomforted the patient. And while the narrow stem portion provides a modicum of flexibility, particularly against torsional forces, the small width of this stem is particularly susceptible to tearing due to shear and tensile forces.

More complicated devices have recently been developed for anchoring naso-gastric tubes to the patient's body. While adhesive tape is still most often used for anchoring the device to the patient, and generally to the patient's nose, attachment to the tube is accomplished by mechanical means such as clamps. U.S. Pat. Nos. 4,120,304, 4,932,943 and 4,986,815 discloses examples of naso-gastric catheter anchoring systems that include clamp type devices. These more complicated means of attachment are commensurately more expensive than adhesive tape and often raise additional concerns. Clamps, for example, tend to pinch and restrict flow through the naso-gastric tube. Alternatively, stiffer tubing may be used to prevent the clamp from pinching off the tube. Such stiff tubing is of course less comfortable to the patient.

Accordingly, a need exists for an inexpensive device for anchoring medical tubing, and particularly naso-gastric tubes, which is comfortable for the patient and is resistant to tearing.

SUMMARY OF THE INVENTION

One aspect of the present invention involves a naso-gastric tube retainer that includes a nose end and a tube end. The nose end and the tube end of the retainer define a longitudinal axis between the ends. The retainer comprises a nose pad at the nose end, which includes a structural layer and an adjacent adhesive layer. A tube attachment section at the tube end also includes a structural layer and an adjacent adhesive layer. A longitudinal neck, which is narrower than either the nose pad or the tube attachment section, connects the nose pad to the tube attachment section. A flexible, substantially inelastic spine extends at least along the length of the neck.

In accordance with another aspect of the present invention, a one-piece naso-gastric retainer is disclosed. The retainer has an upper portion, a lower portion, and a neck portion connecting the upper and lower portions. The retainer comprises a first structural layer, an adhesive layer adjacent the first structural layer, and a second structural layer adjacent the first structural layer. A spine is secured between the first and second structural layers. The spine extends at least the length of the neck portion, is at least as narrow as the neck portion, and comprises a substantially inelastic, flexible material with a tensile strength greater than that of either structural layers.

In accordance with an additional aspect of the present invention, an adhesive, external anchoring device is disclosed for attaching a medical tube to the body of a patient. The device comprises a first end portion, including an adhesive pad for securing the device to a patient, both wider and longer than about 1 inch, to provide a sufficient adhesive area to anchor the device on the patient, while resisting movement of the tube. A second end portion includes an adhesive pad for securing the device to a naso-gastric tube. A neck portion, which is narrower than the first end portion and the second end portion, connects the first end portion to the second end portion. A spine is secured to both the first end portion and the second end portion. The spine extends along at least the length of the neck portion.

Another aspect of the present invention involves a naso-gastric tube retainer, including an upper end portion. The upper end portion includes first means for attaching the retainer to the nose of a patient. A lower end portion includes second means for attaching the retainer to a naso-gastric tube. A flexible, substantially inelastic spine is affixed to and extends between the upper end and lower end portions.

Still another aspect of the present invention involves a medical tube retainer which includes a first pad and a second pad. The retainer includes means for coupling the first and second pads together while allowing movement of the second pad relative to the first pad without producing substantial stress within the retainer.

Further aspects of the present invention will be apparent in view of the disclosure and claims attached below.

BRIEF DESCRIPTION OF THE DRAWINGS

These and other features of the invention will now be described with reference to the drawings of a preferred embodiment which is intended to illustrate and not to limit the invention, and in which.

DETAILED DESCRIPTION OF THE PREFERRED EMBODIMENT

Figure 1:
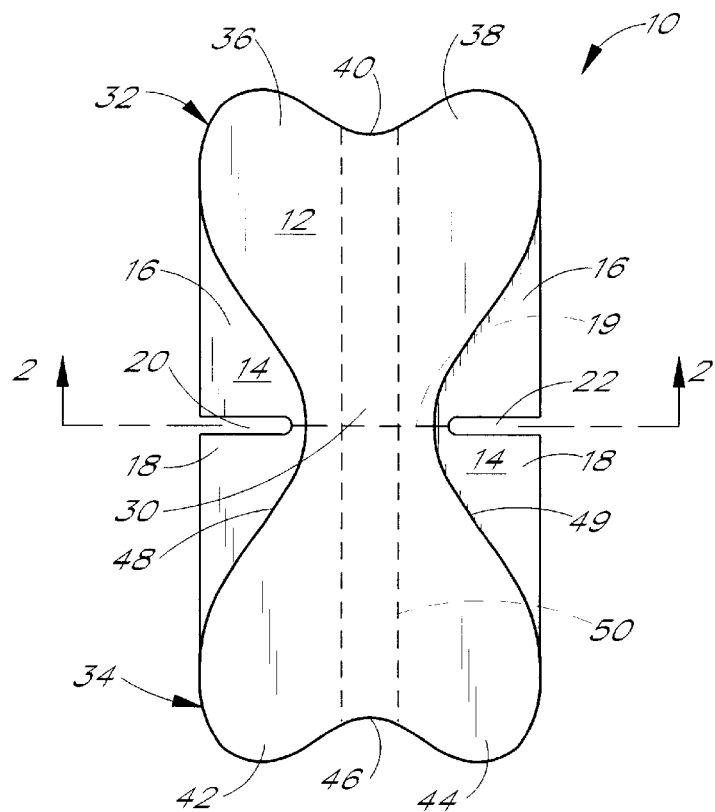
FIG. 1 is a top plan view of a naso-gastric tube retainer, constructed in accordance with an embodiment of the present invention.

FIG. 1 illustrates a tube retainer 10 that is configured in accordance with an embodiment of the present invention. The tube retainer 10 has particular utility in the context of retaining naso-gastric tubes in relation to a patient's face. The tube retainer 10 is accordingly illustrated and described in connection with a naso-gastric tube. It should be understood, however, that the skilled artisan can readily adapt the tube retainer for use in other applications to retain many different types of medical tubes to a patient. For example, the tube retainer may have utility in securing many other types of catheters to other locations on a patient's skin.

From the top plan view of FIG. 1, portions of a removable liner 14 are visible. The liner 10, however, may be coextensive with the shape of the retainer 10 to ease manufacture. The removable liner 14 extends below an area covered by the remainder of the retainer 10. The liner 14 is removed before attachment of the retainer 10 to a patient or a tube.

For convenience of removal prior to using the retainer 10, the liner 14 is desirably provided in two discontinuous liner pieces, an upper liner piece 16 and a lower liner piece 18, with a separation cut 19 extending below the remainder of the retainer. The liner 14 includes left and right notches 20, 22 at the lateral edges of the retainer 10, partially extending across the retainer 10 and partially separating the upper liner piece 16 from the lower liner piece 18. These notches 20, 22 further facilitate alignment of the retainer 10 on the patient, as well as facilitate removal of the liner 14 prior to use of the retainer 10.

Because the illustrated embodiment is symmetrical as seen from the top plan view, use of the terms "upper," "lower," "right" and "left" is essentially arbitrary but will be kept consistent throughout this disclosure. These terms will be used as indicated by the reference numerals, while "top" refers to the side of the retainer 10 visible from the view of FIG. 1.

The retainer 10 narrows at a neck portion 30 of the retainer 10, relative to an upper portion 32 and a lower portion 34 of the retainer 10. For the symmetrical embodiment shown, the upper portion 32 is the mirror image of the lower portion 34 about a lateral axis (coinciding with the cut line 19 which separates the upper liner piece 16 from the lower liner piece 18). The lateral axis thus crosses the retainer 10 at the neck portion 30. The upper portion 32 comprises an upper left lobe 36 and an upper right lobe 38, which extend both laterally and longitudinally from the center of the retainer 10, thereby defining an upper edge 40 which appears concave from the view of FIG. 1. Similarly, the lower portion 34 comprises a lower left lobe 42 and a lower right lobe 44, which extend both laterally and longitudinally from the center of the retainer, thereby defining a concave lower edge 46. Concave left and right edges 48, 49 also result, leading to a minimal width at the lateral axis.

The "neck" or bridge portion 30 of the retainer 10 is defined as that portion of the retainer 10 which structurally connects the upper portion 32 to the lower portion 34, where the upper portion 32 is designed to attach to the patient's skin and the lower portion is designed to attach to a medical tube. For butterfly or hourglass shaped embodiments, such as the illustrated embodiment, the neck may be defined as the narrowest portion of the retainer 10, where width is measured in a direction perpendicular to the longitudinal axis (i.e., laterally as seen from the view of FIG. 1). Where the narrowest portion is simply a line of minimal width rather than an area, as in the illustrated embodiment, the neck portion 30 comprises the area centered around the line of minimal width, of a longitudinal length at least about 5% of the total length of the retainer 10, and bounded by the side edges 48, 49. Desirably, the longitudinal length of the neck portion 30 is at least about 10% of the total retainer length, and more desirably greater than about 20% of the total retainer length. In use upon a patient, at least a part of the neck portion 30 is generally between patient's nose and the medical tube and not attached to either, as will be understood by reference to FIGS. 4 to 6.

It will be understood that neither the particular curvature nor the symmetry of the illustrated embodiment are necessary to achieve the advantages obtained in the naso-gastric tube retainer 10, though both longitudinal and latitudinal symmetry are desirable for aesthetic purposes.

Also shown in the view of FIG. 1 is the outline of a spine 50 that extends longitudinally. The spine 50 provides structural strength in the longitudinal direction to assist in supporting the attached tube when in use on a patient. The spine 50 forms a structural link between the upper portion 32 and the lower portion 34, and accordingly extends at least across the neck portion 30 of the retainer 10. Desirably, the spine 50 extends to the lower edge 46. In the illustrated embodiment, the spine 50 extends the entire length of retainer 10 along the longitudinal axis. Such an arrangement ensures a large surface area over which the spine 50 may be secured to each of the upper portion 32 and the lower portion 34 of the retainer. Means of attaching the spine 50 to the upper and lower portions 32 are described below, along with a discussion of the laminate structure of the illustrated embodiment.

The dimensions of the naso-gastric tube retainer 10 are suitably selected for a desired application, e.g., for attachment to a patient's nose and to a medical tube. For naso-gastric application with adult patients, the longitudinal length of the retainer desirably is between about 2 inches and 5 inches, particularly about 3 inches. Of this length, the length of the upper portion, which must provide adhesion with the patient's skin, is at least about 0.5 inch, desirably greater than about 1.0 inch, and particularly about 1.5 inches. In the illustrated symmetrical embodiment, the lower portion 34 has a similar length. However, it will be understood that a smaller surface area is required for the lower portion 34 to exhibit strong enough adhesion to a medical tube.

The lateral width for the upper portion 32 is also chosen to provide suitable adhesion with a patient's skin and therefore depends upon the length of the upper portion 32 and the adhesive used. Desirably, the width is between about 1 inch and 3 inches, more desirably between about 1.3 inches and 1.7 inches, and particularly about 1.5 inches. For the illustrated symmetrical embodiment, this the lower portion 34 has a similar width. It will be understood, however, that the surface area of the lower portion need not be as great as that of the upper portion 32 in order to provide sufficient adhesion to a medical tube.

In order to provide flexibility, the neck portion 30 should be narrower than the width at the lobes 36, 38 or 42, 44, while wide enough to resist tearing due to the load of the tube. While this dimension may vary greatly depending upon the materials used, the width at the neck portion 30 of the illustrated embodiment may be between about 0.05 inch and 3 inches, desirably between about 0.10 inch and 2 inches, and particularly about 0.5 inch. In light of the additional support provided by the spine 50, however, this dimension is not critical for providing strength.

The width of the spine 50, in turn, also may vary greatly depending upon the materials used and the degree of support provided by the remaining layers. The spine should more narrow than the neck portion 30, so as not to interfere with the bending of the retainer to wrap around the patient's nose or the medical tube. For similar reasons, the spine 50 should be more narrow than the diameter of the tube to which the retainer 10 is to attach. Typical naso-gastric tubes, for example, may have diameters of about 0.3 inch, give or take about 0.1 inch. Accordingly, the width of the spine 50 should be between about 0.05 inch and 1 inch, desirably between about 0.1 inch and 0.5 inch, and particularly less than about 0.3 inches. For the illustrated embodiment, the spine 50 has a width of about 0.25 inch.

It will be understood that the above dimensions are merely exemplary for the illustrated application. Those skilled in the art will readily appreciate that the retainer can have other shapes and sizes.

Figure 2:
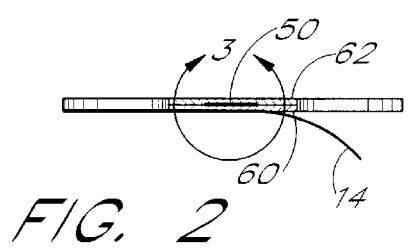
FIG. 2 is a cross-sectional view of the naso-gastric tube retainer, taken along lines 2—2 of FIG. 1.
Figure 3:
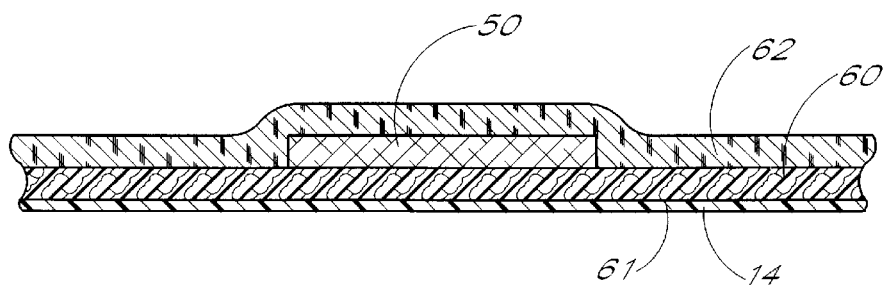
FIG. 3 is an enlarged cross-section view of the portion of the naso-gastric tube retainer within the circle 3—3 of FIG. 2.

As best seen from the cross-sectional views of FIGS. 2 and 3, the illustrated retainer 10 has a laminate structure. A first or bottom structural layer 60 is provided, which is desirably coextensive with the outline of the retainer 10 shown in the plan view of FIG. 1. This bottom layer 60 provides a large surface area for attachment to the patient's nose or to a medical tube. Desirably, the bottom layer 60 comprises a lightweight and flexible structural material. The material can be capable of breathing to allow moisture to escape outwardly, such as breathable foam or tape fabric. An example of a suitable material is a spunlaced polyester nonwoven fabric, available from Avery Dennison in a nominal thickness of about 0.025 inch under the trade name MED 5707.

An adhesive layer 61 underlies the structural layer 60, interposed between the structural layer 60 and the removable liner 14. As will be understood by one of skill in the art, the adhesive 61 desirably comprises a medical grade adhesive. Such adhesives exhibit an affinity for a patient's skin and for the polymeric material of most medical tubes, without irritating the patient's skin. An example of a suitable material is a nonsensitizing porous acrylic copolymer, which is provided on one side of the MED 5707 tape from Avery Dennison, used for the illustrated bottom structural layer 60.

The surface of the liner 14 in contact with the adhesive 61, on the other hand, does not have a high affinity for the adhesive 61, and may be easily peeled away to expose the adhesive layer 61 when the retainer 10 is ready for use. For example, the MED 5707 tape is provided with a densified kraft paper liner with a silicon release coating on one side for reversible adhesion to the adhesive 61.

The illustrated retainer 10 further comprises a second or top layer 62 over the first layer 60. In the illustrated embodiment, the top layer 62 is coextensive with the bottom layer 60, though it need not be. Desirably, the top layer 62 comprises a lightweight and flexible structural material. As with the bottom layer 60, the top layer 62 may also be capable of breathing to allow moisture to escape outwardly, such as foam or tape fabric. Additionally, the top layer 12 is desirably skin-colored for aesthetic reasons, namely to blend in with the patient's skin. An example of a suitable material comprises the same polyester material as the illustrated bottom layer 60. A tan embossed version of the nonwoven polyester fabric is available from Avery Dennison in a nominal thickness of 0.011 inch under the trade name MED 5717P.

The spine 50 is attached to the bottom layer 60 above and below the neck portion 30 (FIG. 1) by means of a laminating adhesive. In the illustrated embodiment, the spine 50 is sandwiched between the top and bottom layers 62, 60, and the layers are desirably attached along the entire length of the spine 50. An adhesive on the bottom surface of the top layer 62 binds the top layer 62 to the bottom layer 60, with the spine 50 secured therebetween. The top layer 62 of the illustrated retainer protects the integrity of the underlying layers, holds the spine in place over the bottom layer, allows outward escape of moisture, and visually blends in with the skin of the patient for aesthetic purposes.

While the spine 50 of the illustrated embodiment is internally located, it will be understood that in other embodiments the spine may be located outside one or more structural layers. For example, the spine may be affixed to the top or the bottom of a structural layer. The spine may also be attached to the structural layer(s) by any other suitable means (e.g., the spine may be sewn to a structural layer).

The spine 50 comprises a material of greater tensile strength than the structural layer 60 or layers 60, 62, to increase resistance to failure due to the longitudinal load exerted by a medical tube. As the layers 60, 62 of the illustrated embodiment comprise polyester fabric with tensile strengths in the range of about 10–12 lbs/inch, the tensile strength of the spine material used in conjunction with the top layer 62 and bottom layer 60 should be greater than about 12 lbs./inch. Desirably, the tensile strength of the spine material in the longitudinal direction is greater than about 15 lbs/inch, more desirably greater than about 25 lbs/inch, and particularly greater than about 40 lbs./inch At the same time, the spine material is flexible with a relatively low modulus of rigidity, such that deflections of the spine 50 during normal use on a patient do not cause substantial internal stress within the retainer 10. Substantial internal stress is that amount of elastic force, created in reaction to deflection of the spine, which causes the retainer to lift from at least a portion of either the patient's skin or the medical tube. It has been determined that materials having a modulus of elasticity of less than about 500,000 p.s.i. do not cause substantial internal stress. For purposes of the present description, such materials are considered substantially inelastic. The spine material of the illustrated embodiment desirably has a modulus of elasticity of less than about 200,000 p.s.i., more desirably less than about 150,000 p.s.i., and particularly less than about 100,000 p.s.i.

It is particularly advantageous for the spine 50 to be substantially inelastic and flexible in directions orthogonal to the longitudinal axis. Specifically, the spine 50 should flexibly bend along the longitudinal axis. For the illustrated embodiment, such flexibility allows the spine 50 to bend around the end of the patient's nose. The spine 50 is also desirably flexible in response to twisting or torsion about the longitudinal axis, to accommodate twisting motions of the tube relative to the patient's body. The spine 50 also desirably bends flexibly along the lateral axis. Such flexibility is particularly desirable where spine is wider than the medical tube so that the wider spine may wrap around the tube.

The spine 50 also exhibits a shear strength sufficient to withstand tearing in the context of its intended use.

Desirably, the shear strength of the spine 50, measured in a propagating or Elmendorf tear, is at least about 0.5 lb./inch, more desirably greater than about 0.8 lb./inch, and particularly greater than about 1.2 lbs./inch.

Materials which have been found suitable for this application as a spine material include polyethylenes, and particularly high-density polyethylenes. The spine 50 of the illustrated embodiment comprises a spun bonded olefin, paper-like material available from E. I. DuPont de Nemours, Inc. under the trade name 1073-B Tyvek™. The illustrated spine 50 has a thickness between 0.001 inch and 0.020 inch, desirably between about 0.004 inch and 0.012 inch, and particularly between about 0.006 inch and 0.010 inch in order to exhibit the desired strength and elasticity set forth above. "Merge 18024" is a specific type of Tyvek™ which is particularly advantageous for use in the medical field, available in a nominal thickness of 0.0073 inch.

Figure 4:
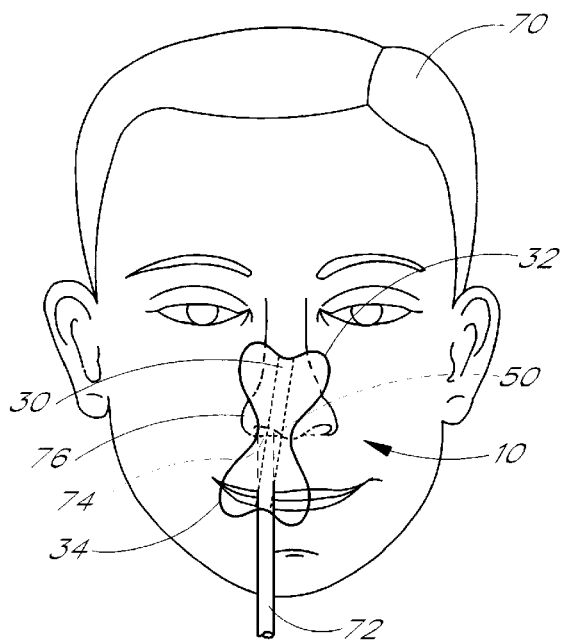
FIG. 4 is a front elevational view of a patient with a medical tube inserted into a nostril of the patient and the naso-gastric tube retainer of FIG. 1 positioned adjacent the patient's nose and the medical tube.
Figure 5:
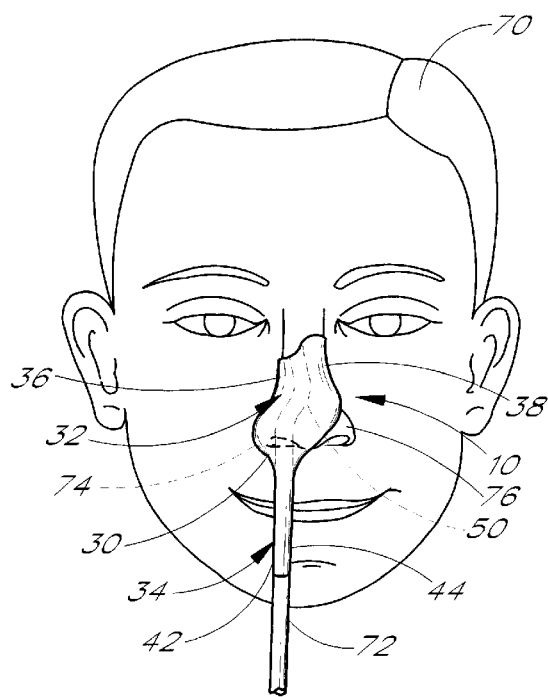
FIG. 5 is a front elevational view of the naso-gastric tube retainer of FIG. 4 wrapped around and adhering to the patient's nose and the medical tube.
Figure 6:
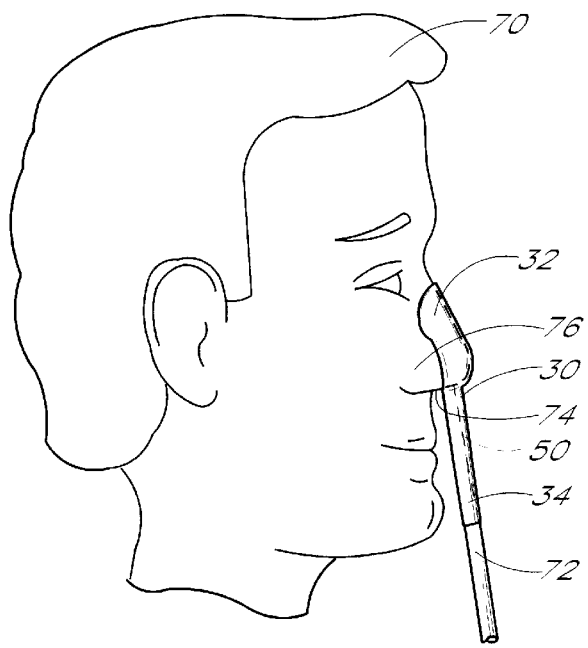
FIG. 6 is a side elevational view of the naso-gastric tube retainer of FIG. 5.

With reference now to FIGS. 4 to 6, the head of a patient 70 is depicted with a naso-gastric tube 72 inserted into the patient's right nostril 74. In FIG. 4, the naso-gastric retainer 10 in accordance with the illustrated embodiment is positioned in front of the patient 70 prior to adhering the retainer to the patient's nose 76 but after peeling away the removable liner 14 (FIG. 1).

In accordance with an embodiment of the invention, the notches 22 or separation cut 19 may be aligned with the tip of the patient's nose 76, such that the upper portion 32 of the retainer 10 is aligned with the patient's nose 76. The lower portion 34 is thereby aligned with the medical tube 72. The upper liner piece 16 (FIG. 1) may be removed first and the upper portion 32 of the retainer 10 attached to the patient's nose 76. The lower liner piece 18 (FIG. 1) may then be removed and the lower portion 34 of the retainer 10 attached to the medical tube 72.

FIGS. 5 and 6 show the naso-gastric tube 72 attached to the patient 70 by way of the naso-gastric tube retainer 10 of the illustrated embodiment. The upper portion 32 of the retainer 10 serves as a nose pad, with the upper lobes 36, 38 wrapped around either side of and adhering to the patient's nose 76 while the concave upper edge 40 conforms to the bridge of the nose 76. The lower portion 34 of the retainer 10 serves as a tube attachment section, with the lower lobes 42, 44 wrapped around and adhering to the medical tube 72.

The upper and lower portions 32, 34 of the retainer 10 are thus sized for adequate adhesion to a patient's skin and a medical tube, respectively. A narrow neck 30 between the upper portion 32 and the lower portion 34 allows flexibility to allow wrapping of the lower portion 34 around a medical tube without causing the retainer 10 to bunch. After application of the retainer 10, the neck 30 allows movement of the attached tube relative to the patient. Unfortunately, the narrow neck portion 30 is particularly susceptible to tearing.

As illustrated, the spine 50 extends across the narrow neck portion 30 of the retainer, providing increased structural support for the tube attachment. The retainer 10 is thus less susceptible to tearing along the neck 30 and the patient 70 is subjected to fewer changes of the retainer 10 for the duration of the treatment. At the same time, the spine 50 is flexible and substantially inelastic, allowing deflection in a horizontal plane without exerting stress on the points of adhesion. Lateral movement of the tube 72 is thereby allowed, while maintaining the tube 72 longitudinally relative to the patient 70.

Although the foregoing invention has been described in terms of an illustrated embodiment, other embodiments will become apparent to those of ordinary skill in the art, in view of the disclosure herein. Accordingly, the present invention is not intended to be limited by the recitation of illustrated embodiment, but is instead intended to be defined solely by reference to the appended claims.

What is claimed is:

1. A naso-gastric tube retainer having a nose end and a tube end defining a longitudinal axis therebetween, the retainer comprising:

a nose pad at the nose end of the retainer, including a structural layer and an adjacent adhesive layer;

a tube attachment section at the tube end of the retainer, including a structural layer and an adjacent adhesive layer;

a longitudinal neck connecting the nose pad to the tube attachment section, wherein the neck is narrower in a dimension perpendicular to the longitudinal axis than each of the nose pad and the tube attachment section; and a flexible, substantially inelastic spine extending at least the length of the neck and being affixed to at least two locations on the neck that are spaced from each other along the longitudinal axis.

2. The naso-gastric tube retainer of claim 1, wherein the spine exhibits a longitudinal tensile strength of at least about 25 lbs./inch.

3. The naso-gastric tube retainer of claim 2, wherein the spine exhibits a longitudinal tensile strength of at least about 40 lbs./inch.

4. The naso-gastric tube retainer of claim 1, wherein the spine has a modulus of elasticity of less than about 150,000 p.s.i.

5. The naso-gastric tube retainer of claim 4, wherein the spine has a modulus of elasticity of less than about 100,000 p.s.i.

6. The naso-gastric tube retainer of claim 1, wherein the spine exhibits a shear strength in a direction perpendicular to the neck of at least about 0.8 p.s.i.

7. The naso-gastric tube retainer of claim 6, wherein the spine exhibits a shear strength in a direction perpendicular to the neck of at least about 1.2 p.s.i.

8. The naso-gastric tube retainer of claim 1, wherein the longitudinal neck includes a structural layer and an adjacent adhesive layer, and the structural and adhesive layers of the nose pad are continuous across the neck with the structural and adhesive layers of the tube attachment section to form a unitary structural layer and a unitary adhesive layer.

9. The naso-gastric tube retainer of claim 1, further comprising a removable liner adjacent to and directly contacting at least one of the adhesive layers of the nose pad and the tube attachment section.

10. The naso-gastric tube retainer of claim 1, wherein the nose pad further includes another structural layer adjacent said structural layer, said structural layer being interposed between said another structural layer and the adhesive layer, and the tube attachment section further including another structural layer adjacent said structural layer of the tube attachment section, said structural liver of the tube attachment section being interposed between said another structural layer and the adhesive layer of the tube attachment section.

11. The naso-gastric tube retainer of claim 10, wherein the spine is interposed between the second structural layer and the structural layer of each of the nose pad and the tube attachment section.

12. The naso-gastric tube retainer of claim 1, wherein the spine is coextensive with the length of the retainer along the longitudinal axis.

13. The naso-gastric tube retainer of claim 1, wherein the spine is narrower than the neck.

14. The naso-gastric tube retainer of claim 1, wherein the structural layers comprise a polyester.

15. The naso-gastric tube retainer of claim 14, wherein the structural layers comprise a spunlaced nonwoven fabric.

16. The naso-gastric tube retainer of claim 1, wherein the spine comprises a high-density polyethylene.

17. A one-piece naso-gastric retainer having an upper portion, a lower portion, and a neck portion connecting the upper portion to the lower portion, the retainer comprising:

a first structural layer;

an adhesive layer adjacent the first structural layer;

a second structural layer adjacent the first structural layer; and a spine secured between the first structural layer and the second structural layer, at least as narrow as the neck portion of the retainer and extending at least the length of the neck portion, comprising a substantially inelastic, flexible material with a tensile strength greater than that of the first and second structural layers.

18. The naso-gastric retainer of claim 17, wherein the neck portion is relatively more narrow than each of the upper portion and the lower portion.

19. The naso-gastric retainer of claim 17, wherein each of the upper and lower portions comprises a right lobe and a left lobe defining a concave longitudinal end of the retainer.

20. The naso-gastric tube retainer of claim 17, wherein the spine has a modulus of elasticity of less than about 100,000 p.s.i.

21. An adhesive, external anchoring device for attaching a medical tube to the body of a patient, comprising:

an first end portion comprising an adhesive pad for securing the device to a patient, having at least a section with a width of greater than about 1 inch and at least a section with a length of greater than about 1 inch;

a second end portion comprising an adhesive pad for securing the device to a naso-gastric tube;

a neck portion, narrower than the first end portion and the second end portion, connecting the first end portion to the second end portion; and a spine fixed to both the first end portion and the second end portion and extending the length of the neck portion.

22. The device of claim 21, wherein the spine comprises a flexible material.

23. The device of claim 21, wherein the spine comprises a substantially inelastic material.

24. The device of claim 23, wherein the spine material has a modulus of elasticity of less than about 150,000 p.s.i.

25. The device of claim 21, wherein the device comprises two layers of structural material and the spine is interposed between the two layers.

26. A naso-gastric tube retainer, comprising:

an upper end portion including first means for attaching the retainer to the nose of a patient;

a lower end portion including second means for attaching the retainer to a naso-gastric tube; and a flexible, substantially inelastic spine affixed to and extending between the upper end and the lower end portions.

27. The naso-gastric tube retainer of claim 26, wherein the first means for attaching the retainer to a nose of a patient comprises a medical grade adhesive layer.

28. A medical tube retainer, comprising:

a first pad for attaching to the skin of a patient;

a second pad for attaching to a medical tube, said second pad being spaced from the first pad; and means for coupling the first and second pads together and for inhibiting the space between the first and second pads from increasing, while allowing all other degrees of movement of the second pad relative to the first pad without producing substantial internal stress in the retainer.

* * * * *

UNITED STATES PATENT AND TRADEMARK OFFICE
CERTIFICATE OF CORRECTION

PATENT NO. : 5,833,663
DATED : Nov. 10, 1998
INVENTOR(S) : Bierman et al.

It is certified that error appears in the above-identified patent and that said Letters Patent is hereby corrected as shown below:

In Claim 10, column 8, line 57, "structural liver" should be --structural layer--.

Signed and Sealed this

Twenty-fourth Day of April, 2001

Attest:

NICHOLAS P. GODICI

Attesting Officer    Acting Director of the United States Patent and Trademark Office